United States Patent [19]

Schrock

[11] 4,197,419

[45] Apr. 8, 1980

[54] TANTALUM CATALYSTS OR CATALYST PRECURSORS

[75] Inventor: Richard R. Schrock, Brighton, Mass.

[73] Assignee: Massachusetts Institute of Technology, Cambridge, Mass.

[21] Appl. No.: 969,896

[22] Filed: Dec. 15, 1978

Related U.S. Application Data

[63] Continuation-in-part of Ser. No. 883,628, Mar. 6, 1978, abandoned.

[51] Int. Cl.$^2$ .......................... C07C 3/21; C07F 9/00
[52] U.S. Cl. .............................. 585/511; 260/429 R; 260/440; 260/446; 260/447
[58] Field of Search .................... 585/511; 260/429 R, 260/440, 446, 447

[56] References Cited

U.S. PATENT DOCUMENTS

| | | | |
|---|---|---|---|
| 3,932,477 | 1/1976 | Schrock | 260/429 R |
| 3,933,876 | 1/1976 | Tebbe | 260/429 R |
| 3,988,332 | 10/1976 | Schrock | 260/429 R |
| 3,992,472 | 11/1976 | Urry | 260/429 R |
| 4,021,429 | 5/1977 | Schrock | 260/429 R |

OTHER PUBLICATIONS

Lebinger et al, JACS, 97, 1596–1597 (1975).

Primary Examiner—C. Davis
Attorney, Agent, or Firm—Arthur A. Smith, Jr.; Paul J. Cook

[57] ABSTRACT

Tantalum catalysts or catalyst precursors of the formula

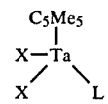

wherein X is a halide, or alkoxide and L is an alkene ($CH_2$=CHR) having from 2 to 20 carbon atoms, react with 1-olefins to give catalysts of the formula

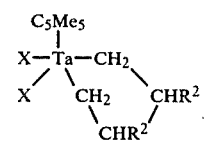

wherein $R^2$ is hydrogen or a $C_1$ to $C_{18}$ alkyl such as methyl, ethyl, or propyl. The catalysts or catalyst precursors selectively dimerize 1-olefins to the two possible disubstituted α-olefin dimers, the ratio of which depends on the nature of R.

24 Claims, No Drawings

TANTALUM CATALYSTS OR CATALYST PRECURSORS

The Government has rights in this invention pursuant to Grant No. CHE76-07410 and IPA-0010 awarded by the National Science Foundation.

REFERENCE TO RELATED APPLICATION

This application is a continuation-in-part application of U.S. patent application Ser. No. 883,628, filed Mar. 6, 1978 and now abandoned.

BACKGROUND OF THE INVENTION

The invention relates to catalysts or catalyst precursors for forming disubstituted α-olefin dimers from a 1-olefin reactant.

Prior to the present invention, there have been no known homegeneous catalysts for converting a terminal olefin selectively to a disubstituted α-olefin dimer at room temperature or above. Known homogeneous dimerization catalysts readily isomerize the initially formed dimer to the thermodynamically more stable internal olefin. It is also known that heterogeneous catalysts such as chromocene on alumina or silica produce 1-butene from ethylene. In addition, other selected dimerization reactions are known. However, these reactions generally are successful for only one olefin, e.g., the use of $KC_8$ to dimerize propylene selectively to 4-methyl-1-pentene.

Accordingly, it would be desirable to provide a homogeneous catalyst system for forming primarily one or both disubstituted α-olefin dimers which can be used with any one of a plurality of unsubstituted or substituted 1-olefin feed compositions.

SUMMARY OF THE INVENTION

This invention provides a class of tantalum catalysts or catalyst precursors for dimerizing 1-olefins primarily to disubstituted α-olefin dimers. The catalysts are useful with ethylene (to produce 1-butene) or substituted $C_2$ to $C_{20}$ olefins, in particular propylene (to produce substantially pure 2,3-dimethyl-1-butene). The catalysts are homogeneous in that they are in the same phase as the reactants under the conditions utilized in the reaction and are represented by the formula:

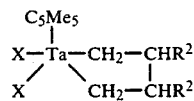

wherein X is a halide, alkoxide, or an alkyl, and $R^2$ is hydrogen or a $C_1$ to $C_{18}$ alkyl such as methyl, ethyl, or propyl.

The precursors to the catalysts of this invention are represented by the formula:

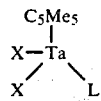  (I)

wherein L is an alkene having from 2 to 20 carbon atoms and which which can be substituted with alkyl or aryl, and X is chloride, bromide, iodide, fluoride, or alkoxide.

The catalysts of this invention are useful for forming disubstituted α-olefin dimers, either a mixture, or substantially one as shown in Table I. Ethylene gives solely 1-butene. Propylene gives 98% 2,3-dimethyl-1-butene. 2,3-dimethyl-1-butene (or 2,3-dimethylbutane) is used as a gasoline additive to improve octane rating.

The precursors I where L=ethylene or propylene can be prepared as follows. Tantalum pentahalide is treated with $Zn(CH_2CMe_3)_2$ at a temperature between about 20° and 40° C. in toluene or pentane to form the compound $Ta(CH_2CMe_3)_2X_3$. The latter compound is reacted with $TlC_5Me_5$ or $LiC_5Me_5$ at a temperature of between about 20° C. and 40° C. in toluene or diethyl ether to give $Ta(C_5Me_5)(CH_2CMe_3)X_3$. $Ta(C_5Me_5)(CH_2CMe_3)X_3$ reacts with one-half mole of $Zn(CH_2CH_3)_2$ or $Zn(CH_2CH_2CH_3)_2$ to give I where L is ethylene or propylene, respectively.

Table I
Disubstituted α-olefin dimers made with a $Ta(C_5Me_5)(propylene)Cl_2$ catalyst in Hexane at 40° C.

| Monomer | Dimers | |
|---|---|---|
| $CH_3CH=CH_2$ | 98% | 2% |
| $CH_3CH_2CH_2CH=CH_2$ | 87% | 13% |
| $CH_3CH_2CH_2CH_2CH=CH_2$ | 85% | 15% |
| $(CH_3)_3CCH_2CH=CH_2$ | 100% | |

The precursors I where L is any other monosubstituted or cis-disubstituted linear or cyclic olefin can be prepared quantitatively by stirring same with $Ta(C_5Me_5)(propylene)Cl_2$ overnight at 25° C.

The catalysts are prepared by the following general reaction. Since this has been shown to be an equilibrium either I or II could be regarded as the catalyst.

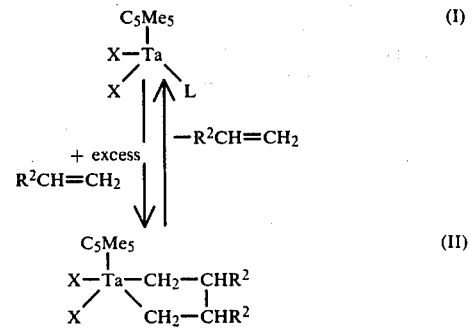

They have been isolated when $R^2$ is hydrogen, methyl, ethyl, or propyl and have been observed by $^{13}C$ NMR when $R^2$ is butyl or neopentyl. The Compounds II, in the presence of a $C_2$–$C_{20}$ olefin, catalytically effect dimerization of the olefin to disubstituted α-olefin dimers as shown in Table I. The reaction of compound I and the olefin is effected in a dry, oxygen-free, inert solvent such as pentane, benzene, decane or the like, at a temperature between about 0° C. and 200° C., preferably between about 20° C. and 100° C. and at a pressure between about 15 psi and 1500 psi, preferably between about 45 psi and 60 psi. The olefin dimer is recovered by distillation after the reaction has been allowed to proceed to completion as indicated by gas chromatography.

Representative compounds prepared by this invention include:

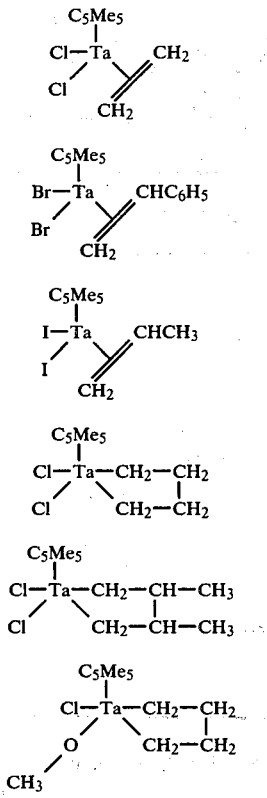

SPECIFIC EMBODIMENTS OF THE INVENTION

The following examples illustrate the present invention and are not intended to limit the same nor be construed as fully dilineating the scope of this discovery.

In order to avoid the presence of molecular oxygen and moisture, all experiments below were carried out in an atmosphere of dry nitrogen gas.

EXAMPLE I

This example illustrates the method for making a compound of the formula

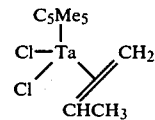

Ta(CH$_2$CMe$_3$)Cl$_4$ (7.92 g) and LiC$_5$Me$_5$ (2.86 g) were stirred in 50 ml of ether for 2 hours. The mixture was filtered and the ether removed from the filtrate in vacuo. The residue was extracted into toluene and the solution filtered. The toluene was removed in vacuo and the crude product recrystallized from ether to give 5.54 g of red-orange crystals. The ether was removed from the filtrate in vacuo and the residue was again extracted into toluene. The solution was filtered and the toluene concentrated until crystals were noted. An equal volume of pentane was added and the solution was stored at −20° C. for 24 h to give another 2.0 g of Ta(C$_5$Me$_5$)(CH$_2$CMe$_3$)Cl$_3$ (overall yield 76%).

$^1$H NMR ($\tau$, C$_6$D$_6$): 8.03 (s, 15, C$_5$Me$_5$), 8.54 (s, 9, CH$_2$CMe$_3$), 8.62 (s, 2, C$\underline{H}_2$CMe$_3$).

A solution of Zn(CH$_2$CH$_2$CH$_3$)$_2$(1.86 g, 12.29 mmol) in 10 ml toluene was rapidly added to a solution of Ta(C$_5$Me$_5$)(CH$_2$CMe$_3$)Cl$_3$ (9.71 g, 19.61 mmol) in 140 ml of toluene at −78° C. After stirring for 5 min at −78° C. the cold bath was removed and the stirred solution was allowed to warm to room temperature. The color changed from orange to purple-red and a dark solid precipitated. The mixture was filtered and the precipitate was extracted with toluene until the filtrate was colorless. The toluene was removed in vacuo from the combined filtrates to give a dark solid which was recrystallized from pentane at −30° C. to give 6.39 g of Ta(C$_5$Me$_5$)(propylene)Cl$_2$ as dark purple crystals (two crops, 76% total yield).

Anal. Calcd for TaC$_{13}$H$_{21}$Cl$_2$: C, 36.39, H, 4.93; Cl, 16.52. Found: C, 36.58; H, 5.06; Cl, 16.66. $^1$H NMR ($\tau$, C$_6$H$_6$): 6.98–8.20 including a large peak at 7.12 (m, 6, CH$_3$CH=CH$_2$), 8.37(s, 15, C$_5$Me$_5$). $^{13}$C NMR (ppm downfield from TMS, d$_8$-toluene, 0° C., $^1$H gated decoupled): 11.6 (q, C$_5$Me$_5$, J$_{CH}$=128 Hz), 27.3 (q, CH$_3$CH=CH$_2$, $^1$J$_{CH}$=125 Hz), 72.3 (t, CH$_3$CH=CH$_2$, $^1$J$_{CH}$=149 Hz), 80.0 (d,CH$_3$CH=CH$_2$, $^1$J$_{CH}$=152 Hz), 117.2(s, C$_5$Me$_5$).

EXAMPLE II

This example illustrates the method of making a compound with the formula

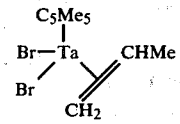

The procedure is virtually identical to that in Example I except Ta(CH$_2$CMe$_3$)Br$_4$ is used in place of Ta(CH$_2$CMe$_3$)Cl$_4$.

EXAMPLE III

This example illustrates the method of making a compound with the formula

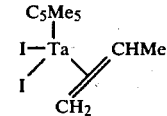

A 0.43 g (1 mmol) sample of Ta(C$_5$Me$_5$)(propylene)Cl$_2$ in 5 ml of tetrahydrofurm was treated with 3.0 g (20 mmol) of anhydrous NaI. Two mols of NaCl were filtered off after ten days and the solvent removed in vacuo. Ta(C$_5$Me$_5$)(propylene)I$_2$ was recrystallized from pentane as very dark red-purple crystals. The yield was essentially quantitative.

EXAMPLE IV

This example illustrates the method of making compounds the formula

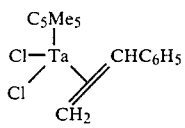

A solution of Ta(C$_5$Me$_5$)(C$_2$H$_4$)Cl$_2$(0.42 g, 1.00 mmol) in 2 ml C$_6$H$_6$ was added to a solution of styrene (0.23 g, 2.20 mmol) in 3 ml C$_6$H$_6$. An $^1$H NMR spectrum recorded after 15 min showed a 1:1 mixture of Ta(C$_5$Me$_5$)(C$_2$H$_4$)Cl$_2$ and Ta(C$_5$Me$_5$)(styrene)Cl$_2$ along with excess free styrene. After 1 h at 25° C. the $^1$H NMR spectrum showed no further change. The mixture was heated to 70° C. for 1 h and the $^1$H NMR spectrum showed almost complete conversion to Ta(C$_5$Me$_5$)(styrene)Cl$_2$. The solvent was removed in vacuo and the solid was recrystallized from toluene/pentane (50/50) at −30° C. to give 0.27 g (54%) dark purple crystals. A GLC analysis suggested there were no styrene/ethylene codimers in the final reaction mixture.

Ta(C$_5$Me$_5$)(propylene)Cl$_2$ (0.86 g, 2.0 mmol) and styrene (0.62 g, 6.0 mmol) were stirred in 10 ml of benzene for 24 h. The benzene was removed in vacuo and the dark solid was extracted into pentane/toluene (50/50) and filtered. Cooling the filtrate to −30° C. for 12 h produced 0.69 g of dark purple crystals. The filtrate was concentrated to a solid in vacuo and recrystallized from pentane/toluene (75/25) at −30° C. to give an additional 0.07 g; overall yield 77% Ta(C$_5$Me$_5$)(styrene)Cl$_2$. The only organic product observed in $^1$H NMR spectra of the reaction mixture was 2,3-dimethyl-1-butene.

$^1$H NMR (τ, C$_6$H$_6$, 90 MHz): 6.56 (t, 1, C$_6$H$_5$CH=CH$_2$, $^3J_{HH}$=12 Hz), 7.00-7.90 (m, 2, C$_6$H$_5$CH=CH$_2$), 8.33(s, 15, C$_5$Me$_5$). $^{13}$C NMR(ppm downfield from TMS, C$_6$D$_6$, $^1$H decoupled): 11.8 (C$_5$Me$_5$), 67.7 (C$_6$H$_5$CH=CH$_2$), 85.2 (C$_6$H$_5$CH=CH$_2$), 118.5 (C$_5$Me$_5$), 125.1, 126.1, 127.3, 149.9 (C$_6$H$_5$CH=CH$_2$).

EXAMPLE V

This example illustrates the method of preparing a compound with the formula

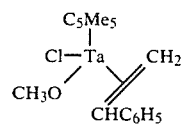

Ta(C$_5$Me$_5$)(styrene)Cl$_2$ (0.49 g, 1 mmol) in 5 ml of diethyl ether was treated with 50 mg of LiOCH$_3$ (slight excess). After one hour the solvent was removed in vacuo and the residue was recrystalized from a mixture of toluene and pentane (1:2) to give deep red crystals of Ta(C$_5$Me$_5$)(styrene)(Cl)(OCH$_3$)(0.30 g, 60% yield).

EXAMPLE VI

This example illustrates the method of preparing a compound with the formula

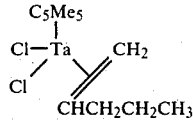

Ta(C$_5$Me$_5$)(propylene)Cl$_2$ (3.43 g, 8.0 mmol) and 1-pentene (2.81 g, 40.0 mmol) were combined in 25 ml of toluene. After stirring for 5 min. the color of the solution changed from red-purple (Ta(III) olefin complex) to orange (Ta(V) metallacycle). The color changed back to red-purple within 12 h and after 24 h the toluene was removed in vacuo to give a dark solid. Recrystallization of the crude product from pentane at −30° C. yielded 3.16 g of dark purple crystalline Ta(C$_5$Me$_5$)(1-pentene)Cl$_2$ (two crops, 86% total yield).

$^1$H NMR (τ, C$_6$H$_6$): 7.00-9.20 including peaks at 7.33(m), 8.90 (br s), 9.02 (s) and 9.13 (s)(m, b 1-pentene), 8.37 (s, C$_5$Me$_5$). $^{13}$C NMR (ppm downfield from TMS, C$_6$D$_6$, $^1$H gated decoupled): 11.8 (q, C$_5$Me$_5$, $^1J_{CH}$=129 Hz), 14.4 (q, CH$_2$=CHCH$_2$CH$_2$CH$_3$, $^1J_{CH}$=125 Hz), 29.0, 43.3 (t, t, CH$_2$=CHCH$_2$CH$_2$CH$_3$, $^1J_{CH}$=125 Hz, 126 Hz), 72.9 (t, CH$_2$=CHCH$_2$CH$_2$CH$_3$, $^1J_{CH}$=142 Hz), 87.0 (d, CH$_2$=CHCH$_2$CH$_2$CH$_3$, $^1J_{CH}$=152 Hz), 117.6 (s, C$_5$Me$_5$).

EXAMPLE VII

This example illustrates the method of preparing a compound with the formula

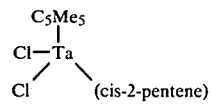

Ta(C$_5$Me$_5$)(propylene)Cl$_2$ (0.64 g, 1.5 mmol) and cis-2-pentene (0.32 g, 4.5 mmol) were stirred in 15 ml of benzene for 24 h. The benzene was removed in vacuo and the dark solid was recrystallized from a minimal amount of pentane at −30° C. to give 0.51 g of dark purple crystalline Ta(C$_5$Me$_5$)(cis-2-pentene)Cl$_2$ (two crops, 74% total yield).

Anal. Calcd. for TaC$_{15}$H$_{25}$Cl$_2$: C, 36.39; H, 4.93; Cl, 15.51. Found: C, 36.58; H, 5.06; Cl, 15.77. $^1$H NMR (τ, C$_6$D$_6$, 90 MHz): 6.30-7.97 including large peaks at 7.13 and 7.19 (m, 7, CH$_3$CH=CHCH$_2$CH$_3$), 8.27 (s, 15, C$_5$Me$_5$), 9.01 (t, 3, CH$_3$CH=CHCH$_2$CH$_3$, $^3J_{HH}$=7 Hz). $^{13}$C NMR (ppm downfield from TMS, C$_6$D$_6$, $^1$H gated decoupled): 11.8 (q, C$_5$Me$_5$, $^1J_{CH}$=128 Hz), 18.9, 19.2 (q, q, CH$_3$CH=CHCH$_2$CH$_3$, $^1J_{CH}$=124 Hz), 27.7 (t, CH$_3$CH=CHCH$_2$CH$_3$, $^1J_{CH}$=127 Hz) 80.2, 87.3 (d, d, CH$_3$CH=CHCH$_2$CH$_3$, $^1J_{CH}$=152 Hz, 148 Hz), 117.9 (s, C$_5$Me$_5$).

EXAMPLE VIII

This example illustrates the method of preparing a compound with the formula

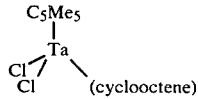

Ta(C$_5$Me$_5$)(propylene)Cl$_2$ (0.43 g, 1.00 mmol) and cyclooctene (0.33 g, 3.00 mmol) were combined in 6 ml benzene. After 12 h at 25° C. the benzene was removed in vacuo. The dark residue was recrystallized from toluene at −30° C. to produce 0.16 g of dark purple crystals. The solvent was removed from the filtrate in vacuo and the solid was recrystallized from pentane/toluene (80/20) to give a second crop of 0.18 g (overall hield 68%) Ta(C₅Me₅)(cyclooctene)Cl₂. The only organic product observed in ¹H NMR spectra of the reaction mixture was 2,3-dimethyl-1-butene.

¹H NMR (τ, C₆D₆): 6.90 to 9.20 with a broad singlet at 7.33 (m, cyclooctene), 8.39 (s, C₅Me₅). ¹³C NMR (ppm downfield of TMS, D₈-toluene, ¹H decoupled): 11.6 (C₅Me₅), 17.9, 26.9, 33.8, 39.4 (aliphatic cyclooctene carbon atoms), 86.0 (olefinic cyclooctene carbon atoms), 117.6 (C₅Me₅).

EXAMPLE IX

This example illustrates the method of preparing a compound with the formula

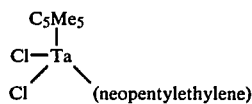

Ta(C₅Me₅)(propylene)Cl₂ (0.43 g, 1.0 mmol) and 4,4-dimethyl-1-pentene (0.35 g, 5.0 mmol) were stirred in 10 ml of toluene for 24 h. The toluene was removed in vacuo and the dark gummy solid was recrystallized from a minimal amount of pentane at −30° C. to give 0.38 g of dark purple crystalline Ta(C₅Me₅)(neopentylethylene)Cl₂ (78%).

¹H NMR (τ, C₆D₆): 6.80–8.50(m, 5, Me₃CCH₂CH=CH₂), 8.25 (s, 15, C₅Me₅), 9.05 (s, 9, Me₃CCH₂CH=CH₂). ¹³C NMR (ppm downfield from TMS, C₆D₆, ¹H gated decoupled): 11.6 (q, C₅Me₅, ¹J$_{CH}$=128 Hz), 29.7 (q, Me₃CCH₂CH=CH₂, ¹J$_{CH}$=124 Hz), 38.1 (s, Me₃CCH₂CH=CH₂), 55.1 (t, Me₃CCH₂CH=CH₂, ¹J$_{CH}$=126 Hz), 75.5 (t, Me₃CCH₂CH=CH₂, ¹J$_{CH}$=150 Hz), 81.6 (d, Me₃CCH₂CH=CH₂, ¹J$_{CH}$=150 Hz), 117.4(s,C₅Me₅).

EXAMPLE X

This example illustrates the method of a compound with the formula

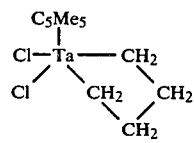

A suspension of Ta(C₅Me₅)(C₂H₄)Cl₂(0.50 g, 1.20 mmol) in 12 ml pentane was stirred under 40 psi ethylene in a glass pressure bottle. Over a period of 15 min the dark suspended solid disappeared and an orange crystalline solid precipitated. The mixture was filtered and the orange solid was rinsed with pentane and dried in vacuo; yield 0.43 g of

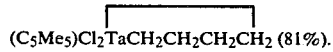

Samples for analysis were recrystallized at −30° C. from methylcyclohexane or pentane/toluene (75/25). NMR spectra were recorded under 1 atmosphere of ethylene.

Anal. Calcd for TaC₁₄H₂₃Cl₂: C, 37.94; H, 5.23; Cl, 16.00. Found: C, 37.63; H, 5.35; Cl, 16.32. ¹H NMR (τ, C₆H₆):

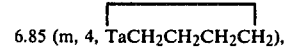

6.85 (m, 4, TaCH₂CH₂CH₂CH₂), 8.20 (s, 15, C₅Me₅),

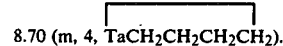

8.70 (m, 4, TaCH₂CH₂CH₂CH₂).

¹H NMR (τ, d₈-toluene, −60° C., 270 MHz): 6.66 (br s, H$_α$), 6.93 (br s, H$_α$'), 8.33 (s, C₅Me₅), 8.78 (br s, H$_β$), 8.90 (br s, H$_β$').

EXAMPLE XI

This example illustrates the method of preparing a compound with the formula

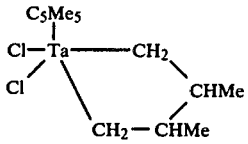

A solution of Ta(C₅Me₅)(propylene)Cl₂(0.65 g, 1.51 mmol) in 15 ml of pentane in a glass pressure bottle was stirred under 40 psi propene. Within 5 min orange crystals of the metallacycle formed in the solution. The propylene connection was shut off and the mixture was stirred for 1 h at 0° C. The light orange supernatant solution was removed by syringe and the product was dried in vacuo for 30 min at 0° C. to give 0.56 g of

(C₅Me₅)Cl₂TaCH₂CHMeCHMeCH₂ (78%).

NMR samples were prepared and recorded at ≦10° C. to prevent thermal decomposition. The solid can be handled at room temperature for short periods (~15 min) without significant decomposition.

¹H NMR (τ, d₈-toluene, 0° C.): 7.05, 8.55, 8.64 and

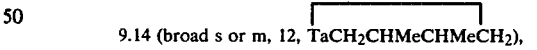

9.14 (broad s or m, 12, TaCH₂CHMeCHMeCH₂), 8.17 (s, 15, C₅Me₅). ¹³C NMR (ppm downfield from TMS, d₈-toluene, ¹H decoupled, 0° C.,): 12.1 (C₅Me₅),

21.0 (TaCH₂CHMeCHMeCH₂), 8.29 (very broad,

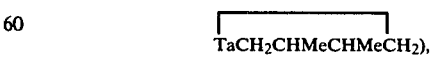

TaCH₂CHMeCHMeCH₂), 122.9 (C₅Me₅), the peaks for the β-carbon atoms are close to the coalesence point.

EXAMPLE XII

This example illustrates the method of preparing a compound with the formula

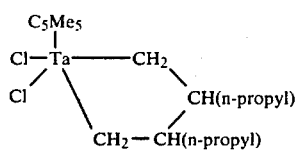

Ta(C$_5$Me$_5$)(1-pentene)Cl$_2$(0.54 g, 1.18 mmol) was dissolved in a minimal amount of pentane and 1-pentene (0.25 g, 3.54 mmol) was added with stirring. After 3 min the orange metallacycle began to crystallize from solution. Shortly thereafter the solution became too thick to stir. Enough pentane/toluene (80/20) was added to dissolve all of the metallacycle. The solution was filtered and cooled to −30° C. for 12 h to give 0.43 g orange crystalline

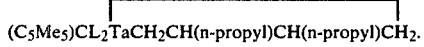

(C$_5$Me$_5$)CL$_2$TaCH$_2$CH(n-propyl)CH(n-propyl)CH$_2$.

The solvent was removed from the filtrate in vacuo and the solid was redissolved in a minimal amount of pentane/toluene (80/20) with a few drops of 1-pentene. This solution was filtered and cooled to −30° C. for 12 h to produce a second crop of 0.04 g (total yield 75%).

$^1$H NMR ($\tau$, d$_8$-toluene, −40° C.): 6.31(br m), 6.97 to 9.81 (complex pattern including broad peak at 8.92), 8.18(C$_5$Me$_5$).

EXAMPLE XIII

This example illustrates the method of preparing a compound with the formula

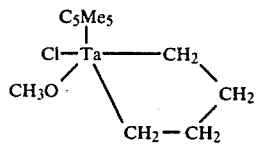

A sample of Ta(C$_5$Me$_5$)(styrene)(Cl)(OCH$_3$)(0.50 g) was suspended in 10 ml pentane (in which it is slightly soluble) in a glass pressure vessel. The vessel was pressurized to 40 psi g and stirred for 1 h to give a pale yellow homogeneous solution. Cooling this solution to −40° for six hours produced pale yellow crystals of

(C$_5$Me$_5$) (OCH$_3$) (Cl)TaCH$_2$CH$_2$CH$_2$CH$_2$ (0.30 g) which were filtered off and dried in vacuo.

EXAMPLE XIV

This example illustrates the method of dimerizing propylene to primarily 2,3-dimethyl-1-butene with Ta(C$_5$Me$_5$)(propylene)Cl$_2$ as the catalyst precursor.

Ta(C$_5$Me$_5$)(propylene)Cl$_2$ (0.11 g, 0.25 mmol) was dissolved in 2.5 ml of hexane in a 20 ml glass pressure bottle containing a small teflon-coated magnetic stir bar. A pressure head equipped with a rubber system for sampling the mixture was clamped to the glass vessel and the vessel was pressurized to 40 psi with propylene and immersed in a stirred bath maintained at 32° C. Samples were withdrawn by syringe at regular intervals, quenched with gaseous oxygen, and analyzed by gas chromatography. 2,3-dimethyl-1-butene and 2-methyl-1-pentene formed steadily in a 98:2 ratio at a rate of 0.0014 M min$^{-1}$ or k$_1$=0.014 min$^{-1}$ since the catalyst concentration is 0.1 M. At 40° k$_1$=0.039 min$^{-1}$ which amounts to about 1 turnover per hour per Ta. The rate increases markedly at higher temperatures ($\Delta$H$^{++}$=19±1 kcal mol$^{-1}$, $\Delta$S$^{++}$=14±3 eu).

The rate determining step of the catalytic reaction is the rate at which

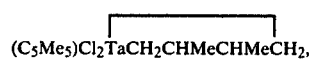

(C$_5$Me$_5$)Cl$_2$TaCH$_2$CHMeCHMeCH$_2$, which forms from Ta(C$_5$Me$_5$)(propylene)C$_{12}$ and propylene, decomposes to give the dimer and two moles of Ta(C$_5$Me$_5$)(propylene)Cl$_2$; −dM/dt=2k$_1$M where M is the concentration of the metallacycle and k$_1$ is the rate constant in the absence of propylene. This rate was measured by $^1$H NMR at four temperatures: k$_1$=0.0015 min$^{-1}$ at 10°, 0.0044 min$^{-1}$ at 20°, 0.014 min$^{-1}$ at 32°, and 0.039 min$^{-1}$ at 40°. The values at 32° and 40° l are identical with those obtained by measuring the rate of the catalytic reaction.

EXAMPLE XV

This example illustrates the method of dimerizing propylene with Ta(C$_5$Me$_5$)(propylene)Br$_2$ as the catalyst precursor.

The procedure is identical to that in Example XIV using 0.11 g Ta(C$_5$Me$_5$)(propylene)Br$_2$ instead of Ta(C$_5$Me$_5$)(propylene)Cl$_2$ as the catalyst precursor. The products were 2,3-dimethyl-1-butene (93%) and 2-methyl-1-pentene (7%) with k$_1$=0.036 min$^{-1}$.

EXAMPLE XVI

This example illustrates the method of dimerizing 1-pentene with Ta(C$_5$Me$_5$)(propylene)Cl$_2$ as the catalyst precursor.

Ta(C$_5$Me$_5$)(propylene)Cl$_2$ (0.11 g) was dissolved in 2.5 ml of hexane. 1-Pentene (1.0 ml) was added and the reaction was maintained at a temperature of 32° C. The products were 2-butyl-3-methyl-1-heptene (85%) and 2-butyl-1-octene (15%) with k$_1$≈0.01 min$^{-1}$.

I claim:

1. A compound of the formula:

wherein X is a halide or alkoxide and L is an alkene having from 2 to 20 carbon atoms.

2. The compound of the formula:

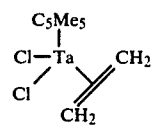

3. The compound of the formula:

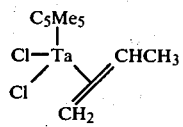

4. The compound of the formula:

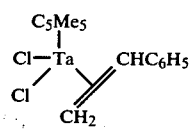

5. The compound of the formula

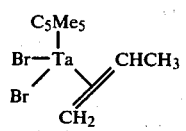

6. The compound of the formula

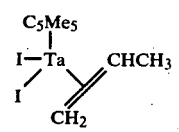

7. The compound of the formula

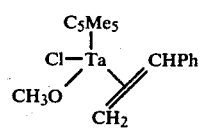

8. The compound of the formula:

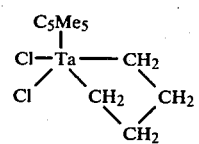

9. The compound of the formula

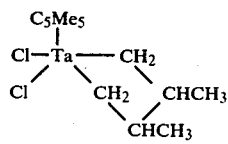

10. The compound of the formula

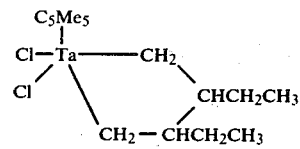

11. The compound of the formula

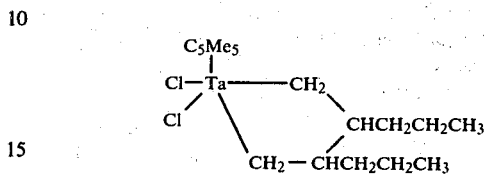

12. The compound of the formula

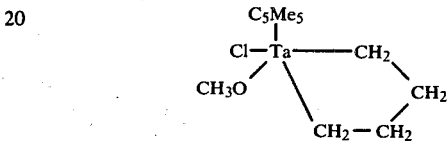

13. The process of forming disubstituted α-olefin dimers selectively which comprises contacting a $C_2$ to $C_{20}$ olefin with the compound in claim 1.

14. The process of forming disubstituted α-olefin dimers selectively which comprises contacting a $C_2$ to $C_{20}$ olefin with the compound in claim 2.

15. The process of forming disubstituted α-olefin dimers selectively which comprises contacting a $C_2$ to $C_{20}$ olefin with the compound in claim 3.

16. The process of forming disubstituted α-olefin dimers selectively which comprises contacting a $C_2$ to $C_{20}$ olefin with the compound in claim 4.

17. The process of forming disubstituted α-olefin dimers selectively which comprises contacting a $C_2$ to $C_{20}$ olefin with the compound in claim 5.

18. The process of forming disubstituted α-olefin dimers selectively which comprises contacting a $C_2$ to $C_{20}$ olefin with the compound in claim 6.

19. The process of forming disubstituted α-olefin dimers selectively which comprises contacting a $C_2$ to $C_{20}$ olefin with the compound in claim 7.

20. The process of forming disubstituted α-olefin dimers selectively which comprises contacting a $C_2$ to $C_{20}$ olefin with the compound in claim 8.

21. The process of forming disubstituted α-olefin dimers selectively which comprises contacting a $C_2$ to $C_{20}$ olefin with the compound in claim 9.

22. The process of forming disubstituted α-olefin dimers selectively which comprises contacting a $C_2$ to $C_{20}$ olefin with the compound in claim 10.

23. The process of forming disubstituted α-olefin dimers selectively which comprises contacting a $C_2$ to $C_{20}$ olefin with the compound in claim 11.

24. The process of forming disubstituted α-olefin dimers selectively which comprises contacting a $C_2$ to $C_{20}$ olefin with the compound in claim 12.

* * * * *